(12) United States Patent
Rabin et al.

(10) Patent No.: US 10,639,497 B2
(45) Date of Patent: May 5, 2020

(54) CONFORMAL TREATMENT DEVICE FOR DELIVERING RADIATION

(71) Applicant: LaserCap Company—Transdermal Cap, Inc., Gates Mills, OH (US)

(72) Inventors: Michael I. Rabin, Gates Mills, OH (US); David Arthur Smith, Shaker Heights, OH (US)

(73) Assignee: LaserCap Company—Transdermal Cap, Inc., Gates Mills, OH (US)

( * ) Notice: Subject to any disclaimer, the term of this patent is extended or adjusted under 35 U.S.C. 154(b) by 798 days.

(21) Appl. No.: 15/204,510

(22) Filed: Jul. 7, 2016

(65) Prior Publication Data

US 2017/0007846 A1    Jan. 12, 2017

Related U.S. Application Data

(60) Provisional application No. 62/189,455, filed on Jul. 7, 2015.

(51) Int. Cl.
| | |
|---|---|
| *A61N 5/06* | (2006.01) |
| *F21V 23/00* | (2015.01) |
| *F21V 21/14* | (2006.01) |
| *F21V 23/02* | (2006.01) |
| *F21S 9/02* | (2006.01) |
| *F21K 9/90* | (2016.01) |
| *F21V 33/00* | (2006.01) |
| *F21V 23/06* | (2006.01) |
| *A61N 5/067* | (2006.01) |

(52) U.S. Cl.
CPC ...... *A61N 5/0617* (2013.01); *A61N 2005/063* (2013.01); *A61N 2005/067* (2013.01); *A61N 2005/0647* (2013.01); *A61N 2005/0652* (2013.01); *A61N 2005/0659* (2013.01); *A61N 2005/0661* (2013.01); *A61N 2005/0662* (2013.01)

(58) Field of Classification Search
CPC combination set(s) only.
See application file for complete search history.

(56) References Cited

U.S. PATENT DOCUMENTS

| | | |
|---|---|---|
| 5,758,947 A | 6/1998 | Glatt |
| 6,267,720 B1 | 7/2001 | Knox et al. |
| 6,325,521 B1 | 12/2001 | Gregg et al. |
| 6,450,941 B1 | 9/2002 | Larsen |
| 7,950,074 B2 | 5/2011 | Loizzo |
| 8,146,607 B2 | 4/2012 | Rabin et al. |
| 8,747,446 B2 | 6/2014 | Chen et al. |
| 9,126,034 B1 | 9/2015 | Deroberts |
| 2007/0179571 A1* | 8/2007 | De Taboada ......... A61N 5/0613 607/88 |

(Continued)

FOREIGN PATENT DOCUMENTS

| | | |
|---|---|---|
| EP | 2486955 A1 | 8/2012 |
| WO | 2006/125367 | 11/2006 |
| WO | 2010/090590 | 8/2010 |

*Primary Examiner* — Scott Luan
(74) *Attorney, Agent, or Firm* — Renner, Otto, Boisselle & Sklar, LLP

(57) ABSTRACT

A treatment device configured to illuminate a surface of a 3D skin surface when positioned adjacent the illuminated surface of the 3D skin surface. The treatment device includes a number of linear light source strips to conformally illuminate the 3D skin surface.

38 Claims, 11 Drawing Sheets

(56) References Cited

U.S. PATENT DOCUMENTS

| | | |
|---|---|---|
| 2007/0256212 A1 | 11/2007 | Rabin |
| 2009/0012586 A1 | 1/2009 | Kepecs |
| 2010/0106077 A1 | 4/2010 | Rabin et al. |
| 2010/0242155 A1 | 9/2010 | Carullo, Jr. |
| 2011/0092863 A1 | 4/2011 | Kim et al. |
| 2016/0263395 A1* | 9/2016 | Siegel .................. A61B 5/4836 |

* cited by examiner

CONFORMAL TREATMENT DEVICE FOR DELIVERING RADIATION

TECHNICAL FIELD

The present disclosure relates generally to a therapeutic device that delivers optical energy to human body tissues and in particular to a treatment device configured to illuminate a three-dimensional (3D) skin surface.

BACKGROUND

Light therapy has been shown as an effective treatment to stimulate hair growth and to treat certain skin disorders. For example, the publication Avci, Pinar, et al. "Low-level laser (light) therapy (LLLT) for treatment of hair loss." *Lasers in surgery and medicine* 46.2 (2014): 144-151 identifies many applications of low level light therapy (LLLT) including wound healing, fat metabolism, brain stimulation, psoriasis treatment and hair regrowth. There are devices currently available in the market for delivering low level light therapy in order to stimulate hair growth. The available devices employ either a single or segmented substrate including multiple light sources for delivering light having a known therapeutic effect.

SUMMARY OF INVENTION

The available LLLT devices suffer from many problems, including rigid substrates, flexible substrates that do not conformally cover the scalp, inability to bypass hair and deliver light to the scalp of patients with thinning hair, restricted airflow to the light source arrays, high cost to manufacture, and discomfort to the patient.

The present disclosure provides a treatment device including a number of linear light source strips that are arranged to form a 3D surface, such that the combined light emitted by light sources of the linear light source strips illuminate the surface of the 3D skin surface.

According to one aspect of the disclosure, there is provided medical or cosmetic treatment device configured to illuminate a surface of a 3D skin surface when positioned adjacent the illuminated surface of the 3D skin surface. The medical or cosmetic treatment device includes a plurality of linear light source strips. Each linear light source strip includes a plurality of light sources. Each linear light source strip has an origination point and a termination point. For a given linear light source strip, each light source of the given linear light source strip is arranged between the origination point and the termination point. The device also includes controller circuitry electrically connected to each of the plurality of linear light source strips, wherein the controller circuitry is configured to provide electrical power to each of the plurality of linear light source strips. The plurality of linear light source strips are arranged to form a three-dimensional (3D) surface such that the combined light emitted by the light sources of the plurality of linear light source strips illuminates the surface of the 3D skin surface when positioned adjacent the 3D skin surface.

Alternatively or additionally, the plurality of linear light source strips are arranged in a fan like shape and the controller circuitry comprises a hub of the fan like shape.

Alternatively or additionally, the controller circuitry comprises two more distinct sub-controllers and the sub-controllers each comprise the hub of a subgroup of the plurality of linear light source strips.

Alternatively or additionally, within the fan like shape, the linear light source strips are arranged in a palmate pattern on a concave interior surface of a supporting 3D concave shape.

Alternatively or additionally, the linear light source strips have different lengths.

Alternatively or additionally, the spacing between at least some of the adjacent linear light source strips is adjustable.

Alternatively or additionally, the termination point of a majority of the plurality of linear light source strips are attached to a joining member.

Alternatively or additionally, the joining member comprises an arc-shaped slice.

Alternatively or additionally, the plurality of linear light source strips are arranged such that the plurality of linear light source strips do not overlap.

Alternatively or additionally, the 3D surface is adjustable to illuminate the surface of 3D skin surfaces having different sizes.

Alternatively or additionally, the controller circuitry is configured to individually and separately provide electrical power to each linear light source strip.

Alternatively or additionally, the controller circuitry is configured to provide power to the plurality of linear light source strips, such that the plurality of linear light source strips are illuminated in a pattern where all of the plurality of linear light source strips are not simultaneously illuminated.

Alternatively or additionally, the device also includes a power supply configured to supply electrical power to the controller circuitry.

Alternatively or additionally, the power supply comprises a battery or a connecter to an external power supply.

Alternatively or additionally, the power supply comprises a battery located adjacent the controller circuitry.

Alternatively or additionally, the plurality of light sources are either laser diodes, light emitting diodes (LEDs), or a combination of laser diodes and LEDs.

Alternatively or additionally, the plurality of light sources emit electromagnetic radiation within a range of wavelengths or set of wavelengths having a known therapeutic effect.

Alternatively or additionally, the plurality of light sources emit electromagnetic radiation having wavelengths chosen from at least one of the set of ultraviolet, visible, and infrared.

Alternatively or additionally, the plurality of light sources collectively emit electromagnetic radiation having wavelengths in two different wavelength ranges, each light source emitting light in only one of the two different wavelength ranges.

Alternatively or additionally, the two different wavelength ranges are chosen from at least one of the set ultraviolet, visible, and infrared.

Alternatively or additionally, the device includes a light diffuser. The light diffuser includes a surface. The plurality of linear light source strips are mounted adjacent the surface of the light diffuser. Each light source of the plurality of linear light source strips emits electromagnetic radiation towards the diffuser. The light diffuser is configured to reflect, scatter, and/or refract light in order to provide uniform illumination to the surface of the 3D skin surface.

Alternatively or additionally, the device includes a diffuser. The diffuser is mounted adjacent an interior convex surface of the 3D surface. Each light source of the plurality of linear light source strips emits electromagnetic radiation towards the diffuser. The diffuser is configured to scatter and/or refract light in order to provide uniform illumination to the surface of the 3D convex skin surface.

Alternatively or additionally, the treatment device additionally includes an inner layer comprising a surface including a plurality of light covering elements positioned to receive the light sources of the linear light source strips. Each light covering element forms a structure shaped to receive a light emission end of one of the light sources of the plurality of linear light source strips.

Alternatively or additionally, the light covering elements are configured to act as light guides to direct light emitted by the light sources away from the light sources.

According to another aspect of the disclosure, there is provided a method of manufacturing treatment device configured to illuminate a surface of a 3D skin surface. The method includes overlying an adhesive layer on a back surface of an array of a plurality of linear light source strips, such that the adhesive layer adheres to the back surface of the array. Each linear light source strip of the plurality of linear light source strips includes a plurality of light sources connected to a substrate. The substrate forms a back surface of the array. Each light source includes a light emission end and a base end opposite the light emission end. The base end of each light source is connected to the substrate. Each of the plurality of linear light source strips are connected to an origin point of the array. The linear light source strips fan out from the origin point. The adhesive layer includes a first surface that adheres to the back surface of the array and a second surface opposite the first surface. The method also includes overlying an outer layer on the second surface of the adhesive layer. The method further includes connecting controller circuitry to the array. The controller circuitry provides electrical power to the light sources of the array. The method additionally includes connecting each linear light source strip at a terminating end opposite the origin point, such that the linear light source strips of the array are arranged to form a three-dimensional (3D) surface such that the combined light emitted by the light sources of the plurality of linear light source strips illuminates the surface of the 3D skin surface when positioned adjacent the 3D skin surface.

Alternatively or additionally, the method also includes overlying an inner layer on a front surface of the array, wherein the inner layer comprises a surface including a plurality of light covering elements positioned to receive the light sources of the array.

Alternatively or additionally, overlying the inner layer on the front surface of the array includes positioning the light emission end of each of the light sources of the array into a light covering element projecting from the surface of the inner layer.

Alternatively or additionally, the adhesive layer includes a pressure sensitive adhesive on the first surface that is applied to the back surface of the array and a heat activated adhesive or a second pressure sensitive adhesive on the second surface that is applied to the outer layer.

Alternatively or additionally, the method includes heat curing the adhesive layer after connecting each linear light source strip at the terminating end to adhere the outer layer and the adhesive layer.

Alternatively or additionally, at least one of the array, adhesive layer, or outer layer is die cut or laser cut.

Alternatively or additionally, each linear light source strip is connected at the terminating end to a joining member.

Alternatively or additionally, the method also includes, prior to connecting each linear light source strip to the joining member, cutting the combination of the array, adhesive layer, and outer layer. The cutting includes forming a joining hole at the terminating end of each linear light source strip opposite the origin point, wherein each linear light source strip is joined to the joining member via the joining hole.

Alternatively or additionally, prior to cutting the array, adhesive layer, and outer layer, the array of linear light source strips comprises a sheet including a plurality of light sources positioned such that the plurality of light sources form the plurality of linear light source strips when the array is cut.

Alternatively or additionally, the joining member comprises an arc-shaped slice and connecting the linear light source strips to the joining member comprises positioning a terminating point of each linear light source strip in a receiving structure of the joining member such that projections located within the receiving structure of the joining member interact with the joining hole of each linear light source strip.

Alternatively or additionally, the joining member comprises an arc-shaped slice; and connecting the linear light source strips to the joining member comprises positioning the terminating end of each linear light source strip in a receiving structure of the joining member such that the linear light source strips are maintained in the formed 3D surface.

Alternatively or additionally, the array of linear light source strips is formed by affixing separate linear light source strips to an origin structure.

Alternatively or additionally, the array of linear light source strips is symmetric about a central axis perpendicular to one or more base linear light source strips.

Alternatively or additionally, the controller circuitry is connected to the light source strip array near the origin point.

Alternatively or additionally, the controller circuitry is connected to the array by electrically connecting the controller circuitry to electrical leads supplying power to each of the plurality of linear light source strips.

Alternatively or additionally, the controller circuitry is physically connected to the outer layer.

The foregoing and other features of the invention are hereinafter fully described and particularly pointed out in the claims, the following description and annexed drawings setting forth in detail certain illustrative embodiments of the invention, these embodiments being indicative, however, of but a few of the various ways in which the principles of the invention may be employed.

Features that are described and/or illustrated with respect to one embodiment may be used in the same way or in a similar way in one or more other embodiments and/or in combination with or instead of the features of the other embodiments.

DETAILED DESCRIPTION OF THE INVENTION

Figure 1A:
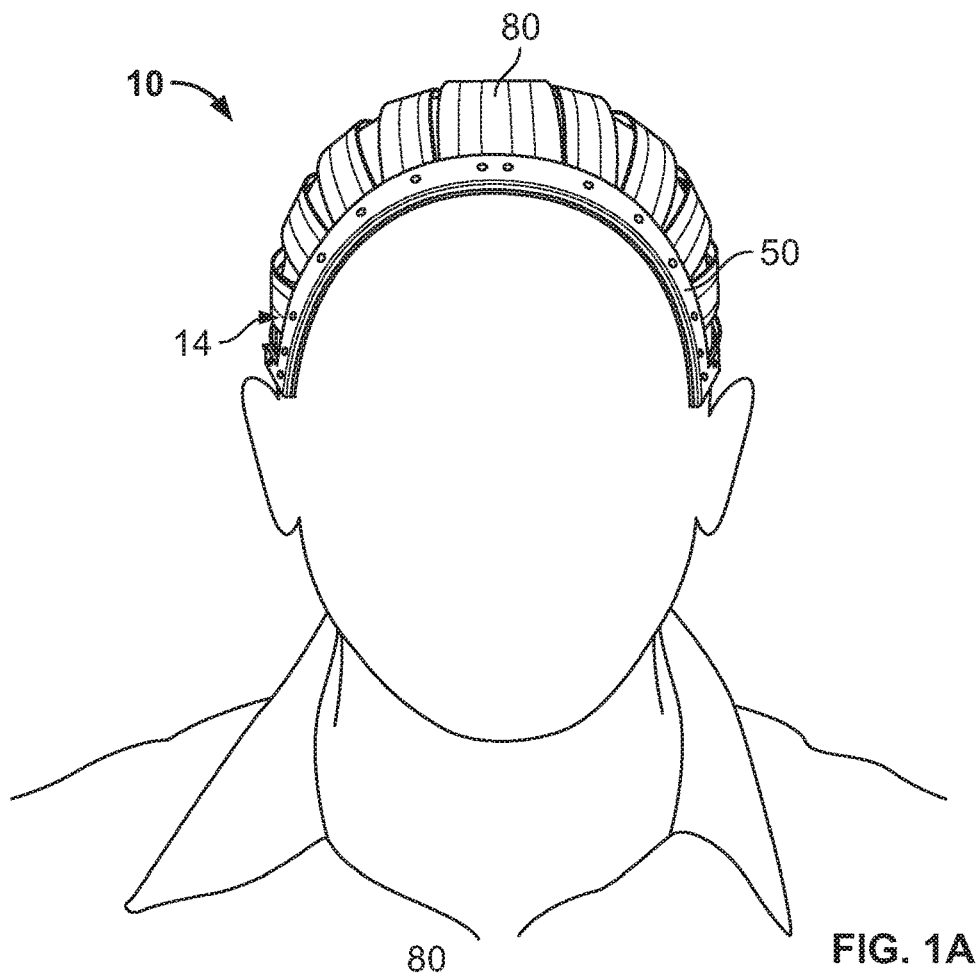
FIG. 1A is a front perspective view of a treatment device.

The present disclosure provides a treatment device configured to illuminate a surface of a 3D skin surface when positioned adjacent the illuminated surface of the 3D skin surface. The treatment device includes a number of linear light source strips positioned to conform to and conformally illuminate a user's scalp.

Turning to FIGS. 1A-1D, a treatment device 10 including an array 14 and controller circuitry 30 is shown. The array 14 includes a plurality of linear light source strips 20. Each of the linear light source strips 20 includes a plurality of light sources 22. The linear light source strips 20 are arranged, upon final assembly, to form a three-dimensional (3D) surface 12 such that the combined light emitted by the light sources 32 of the plurality of linear light source strips 20 illuminates the surface of a 3D skin surface when positioned adjacent the 3D skin surface. For example, the treatment device 20 may be placed on a patient's head such that the light emitted by the light sources 22 illuminates the patient's scalp. The electromagnetic radiation emitted by the light sources 22 may be selected to have a therapeutic effect. For example, the emitted electromagnetic radiation may fall within a range of wavelengths shown to stimulate hair growth.

Figure 2:
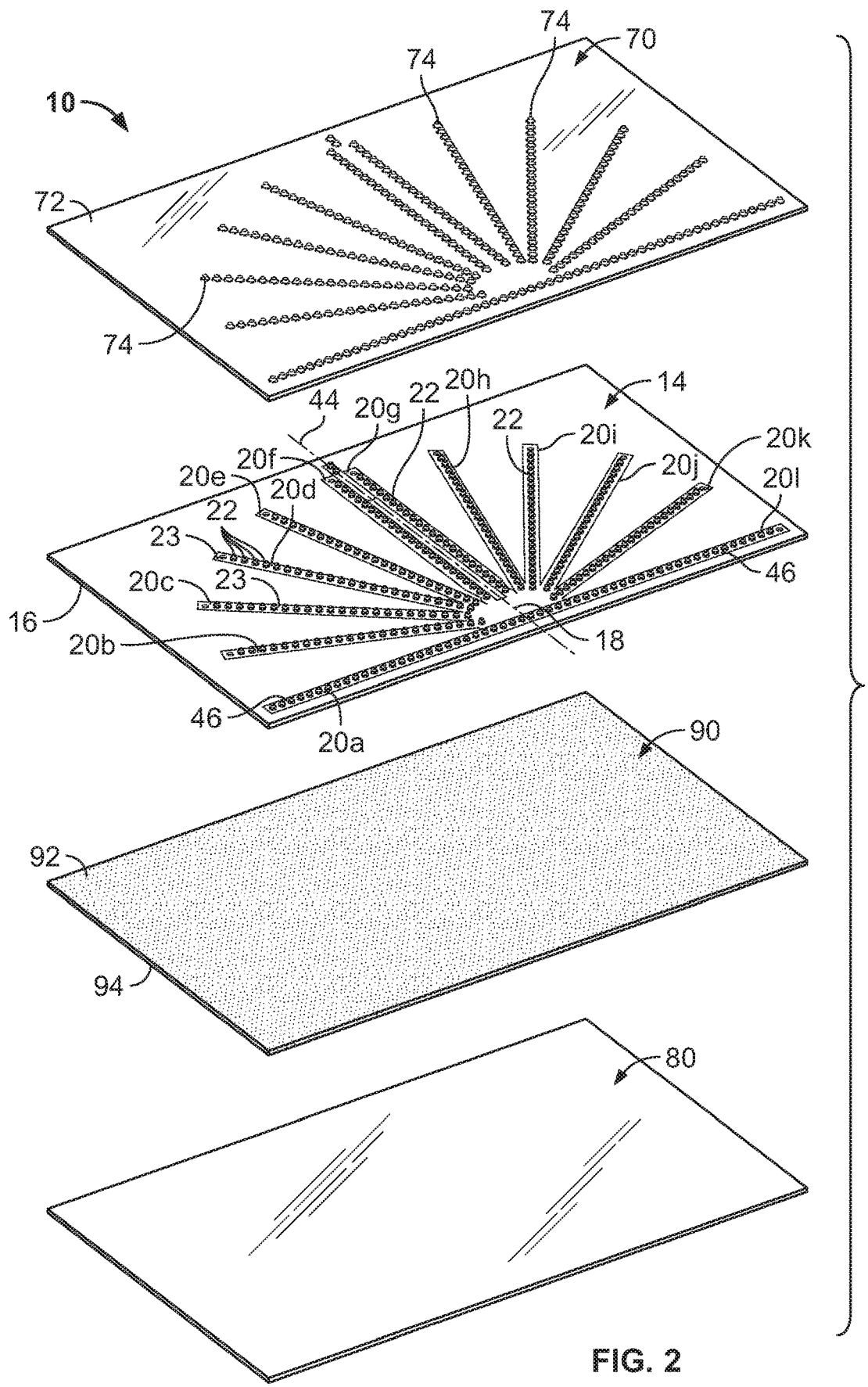
FIG. 2 is an exploded view of the treatment device of FIGS. 1A and 1B during manufacture.
Figure 5:
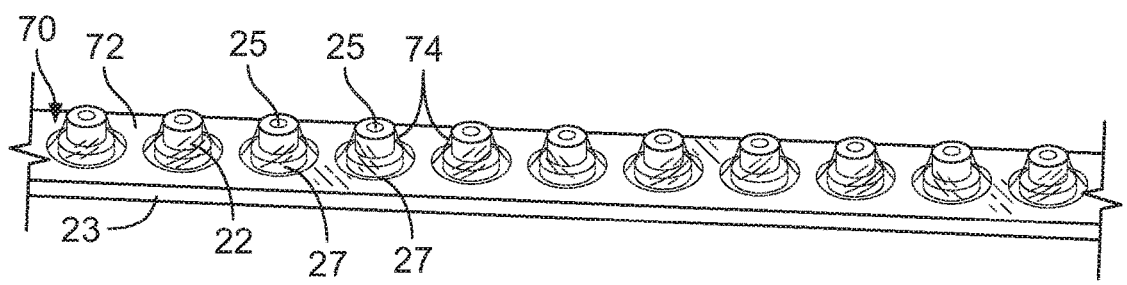
FIG. 5 is a close up view of the inner layer of FIG. 4 and linear light source strips of FIG. 3A.

With reference to FIG. 2, a two-dimensional layout view of an exemplary device prior to final segmentation assembly and shaping into three dimensions is shown. In FIG. 2, each of the plurality of linear light source strips 20 includes a plurality of light sources 22 connected to a substrate 23. The substrate 23 forms a back surface 16 of the array 14 as will be described. With reference to FIG. 5, each light source 22 includes a light emission end 25 and a base end 27 opposite the light emission end 25. The base end 27 of each light source 22 is connected to the substrate 23.

The linear light source strips 20 may be individually manufactured flexible strips attached to one or more substrates 23 as will be described with reference to FIG. 3E. Alternatively, as described below, a two-dimensional light source pattern may be formed from the plurality of light sources 22 being attached to a single substrate 23 and cutting the single substrate 23 into a fan like pattern to form the linear light source strips 20.

Each of the plurality of linear light source strips 20 are connected to an origin point 18 or origin area of the array.

The linear light source strips 20 may be positioned to fan out from the origin point 18. For example, the array of linear light source strips 20 may be symmetric about a central axis 44. Optionally, additional linear light source strip 20 may be included to provide illumination of more complex 3-D skin surfaces.

Figure 3A:
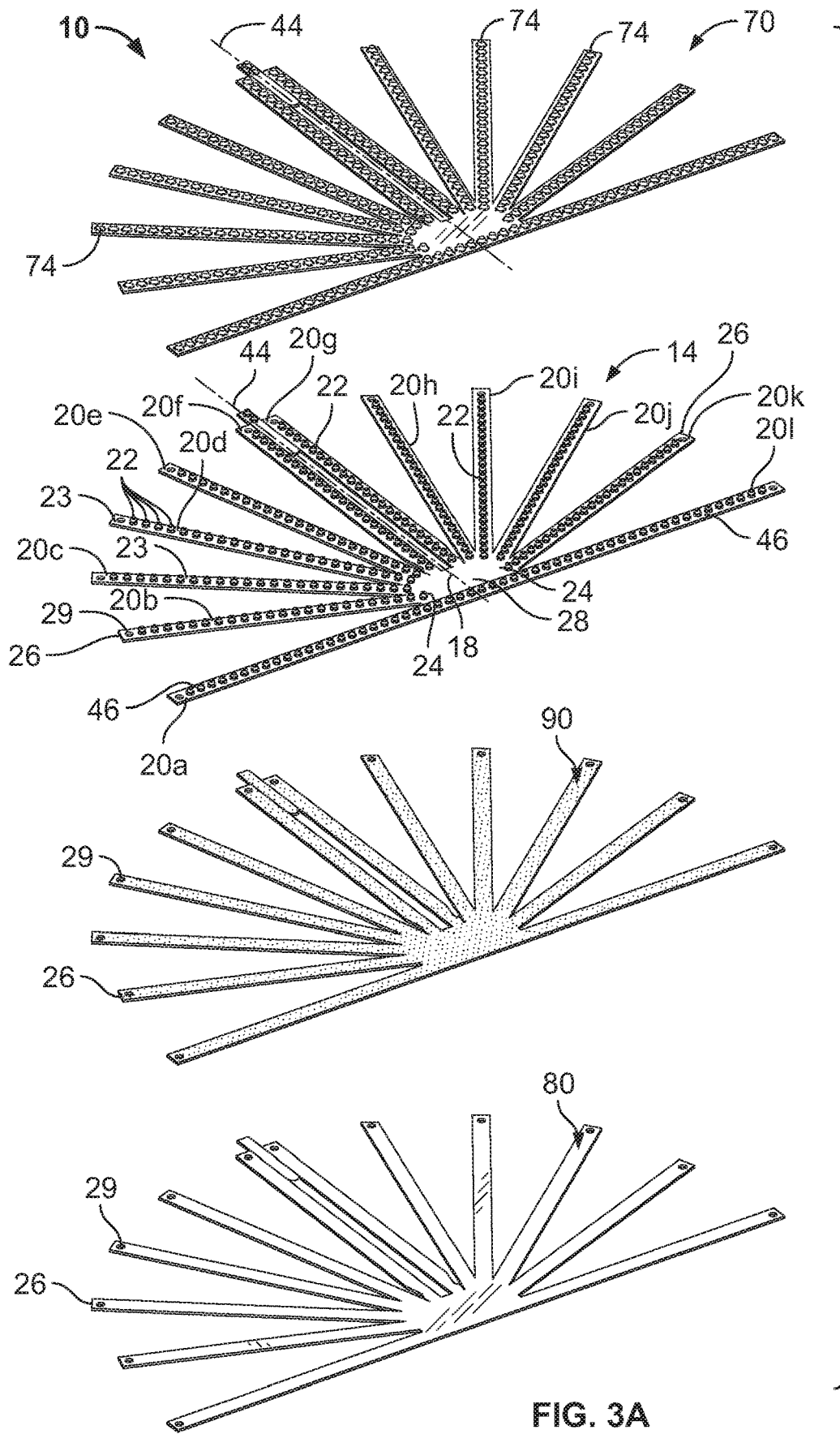
FIG. 3A is an exploded view of the treatment device of FIG. 2 after cutting during manufacture.
Figure 3B:
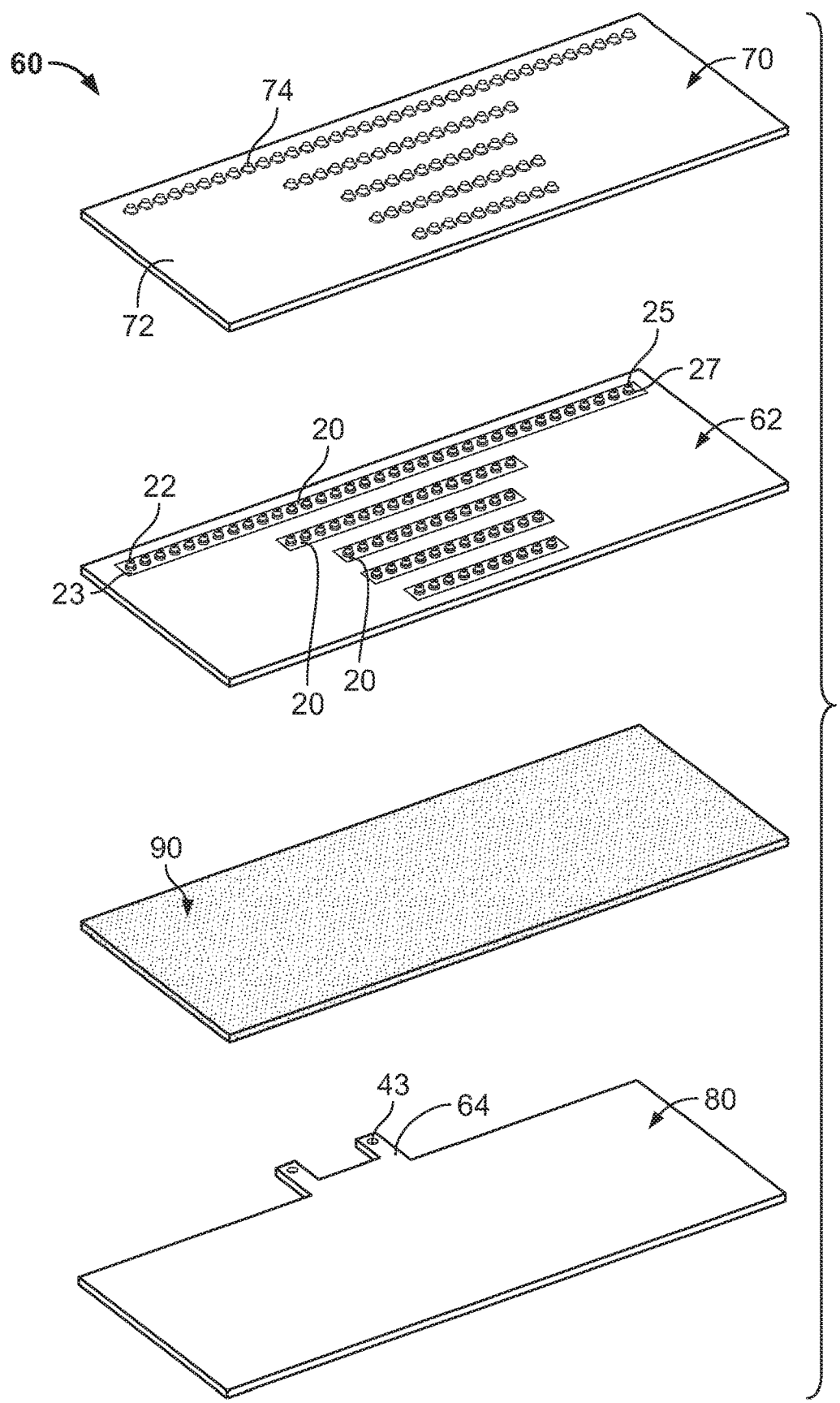
FIG. 3B is an exploded view of an extension panel of the treatment device.
Figure 3C:
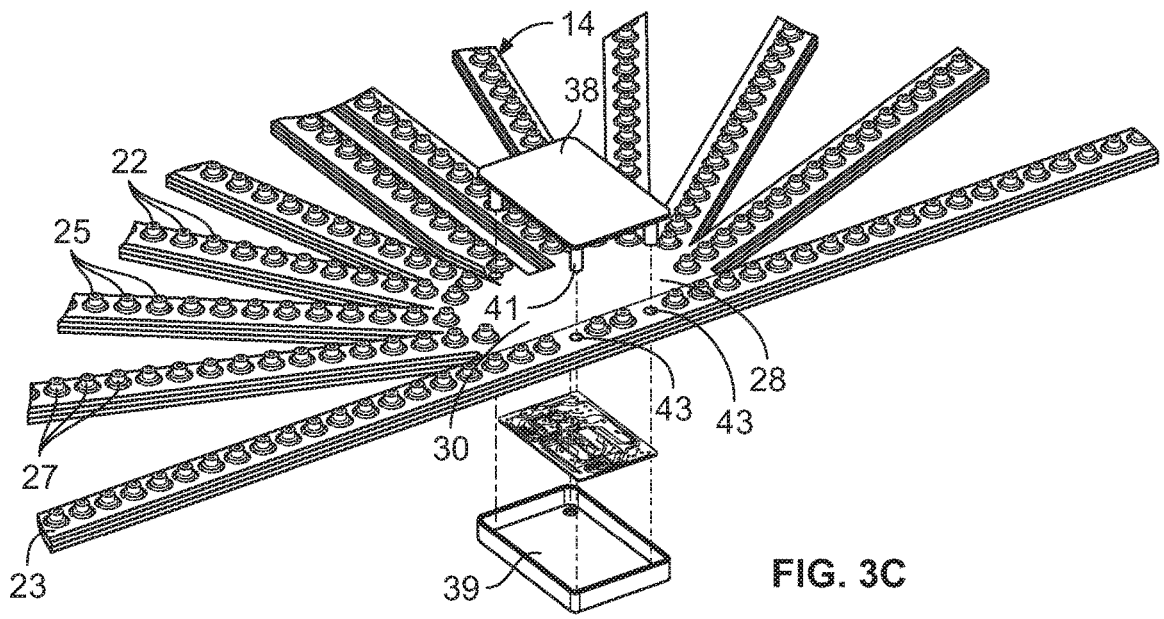
FIG. 3C is an exploded close up view of the treatment device of FIG. 3A, a housing, and a controller.

As shown in FIGS. 3A and 3C, the plurality of linear light source strips 20 may be arranged in a fan like shape and the controller circuitry 30 may comprise a hub 28 of the fan like shape. A fan like shape may refer to a palmate pattern where one or more linear light source strips 20 radiate out from the hub 28.

The linear light source strips 20 may be contained on their own flexible substrates 23 to permit shaping to a desired 3-D shape. Examples of flexible linear light source strips are LED lighting strips available from Sylvania. Additionally, the spacing between at least some of the adjacent linear light source strips 20 may be adjustable. For example, the 3D surface may be adjustable to illuminate the surface of 3D skin surfaces having different shapes and/or sizes. The treatment device 10 may also be deformable such that the linear light source strips 20 are repositionable to allow adjustment to the field of illumination provided by the light sources 20 of the treatment device 20.

As will be understood by one of ordinary skill in the art, the plurality of linear light source strips 20 being connected to the hub or origin point 18 may refer to the plurality of linear light source strips 20 being physically connected and/or electrically connected to the hub or origin point 18.

Each linear light source strip 20 has an origination point 24 and a termination point 26. For a given linear light source strip 20, each light source 22 of the given linear light source strip 20 is arranged between the origination point 24 and the termination point 26. For example, each light source 22 of a given linear light source strip 20 may be arranged along a line between the origination point 24 and the termination point 26. However, as will be understood by one of ordinary skill in the art, each light source 22 of a given linear light source strip 20 may not be arranged along a line between the origination point 24 and the termination point 26. For example, the light sources 22 for a given linear light source strip 20 may be arranged such that some of the light sources 22 are arranged in a staggered pattern as opposed to along a straight line. Arranging the light sources 22 in this non-linear manner may improve the pattern of light delivery such that the light emitted by the light sources 22 more uniformly illuminates a patient's scalp. The origination point 24 and termination point 26 are reference points and may not correspond to distinct physical locations on each linear light source strip 20.

The linear light source strips 20 may have different lengths and/or different numbers of light sources 20.

As will be understood by one of ordinary skill in the art, the light sources 22 may comprise any suitable structure for emitting light. For example, the light source 22 may comprise at least one of light emitting diodes (LEDs), laser diodes, leaky optical fiber illuminated by one or more LEDs or laser diodes, or any other suitable source of light. In one example, the plurality of light sources 22 are either laser diodes, LEDs, or a combination of laser diodes and LEDs.

The plurality of light sources 22 may emit electromagnetic radiation within a range of wavelengths or set of wavelengths having a known therapeutic effect. For example, the plurality of light sources 22 may emit electromagnetic radiation having wavelengths chosen from at least one of the set of ultraviolet, visible, and infrared. The plurality of light sources 22 may collectively emit electromagnetic radiation having wavelengths in two or more different wavelength ranges, with each light source 22 emitting light in only one or more than one of the two or more different wavelength ranges. Reference to "light" in this disclosure may refer to any suitable wavelength of electromagnetic radiation, including infrared and ultra-violet electromagnetic radiation.

As shown in FIGS. 2 and 3A, the linear light source strips 20 of the array 14 may be arranged on an outer layer 80. For example, the linear light source strip 20 may be arranged on a concave interior surface 40 of a supporting 3D concave shape formed by the outer layer 80 as shown in FIG. 1D. The outer layer 80 may provide structural support to the array 14. The plurality of linear light source strips 20 may be arranged on the outer layer 80 such that the plurality of linear light source strips 20 do not overlap. The outer layer 80 may be cut to match the array 14 or the outer layer 80 may extend beyond the linear light strips 20. The outer layer 80 may be made from any suitable material, such as a rigid or flexible polymer.

Figure 1B:
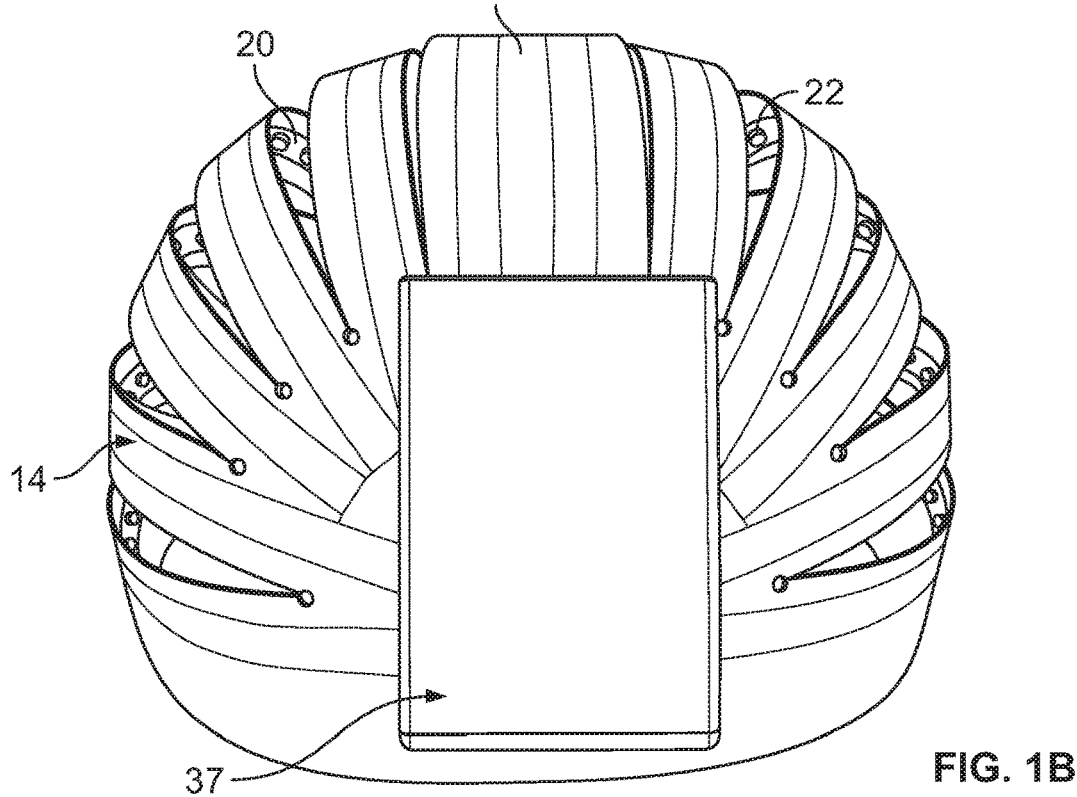
FIG. 1B is a back perspective view of the treatment device of FIG. 1A.
Figure 1C:
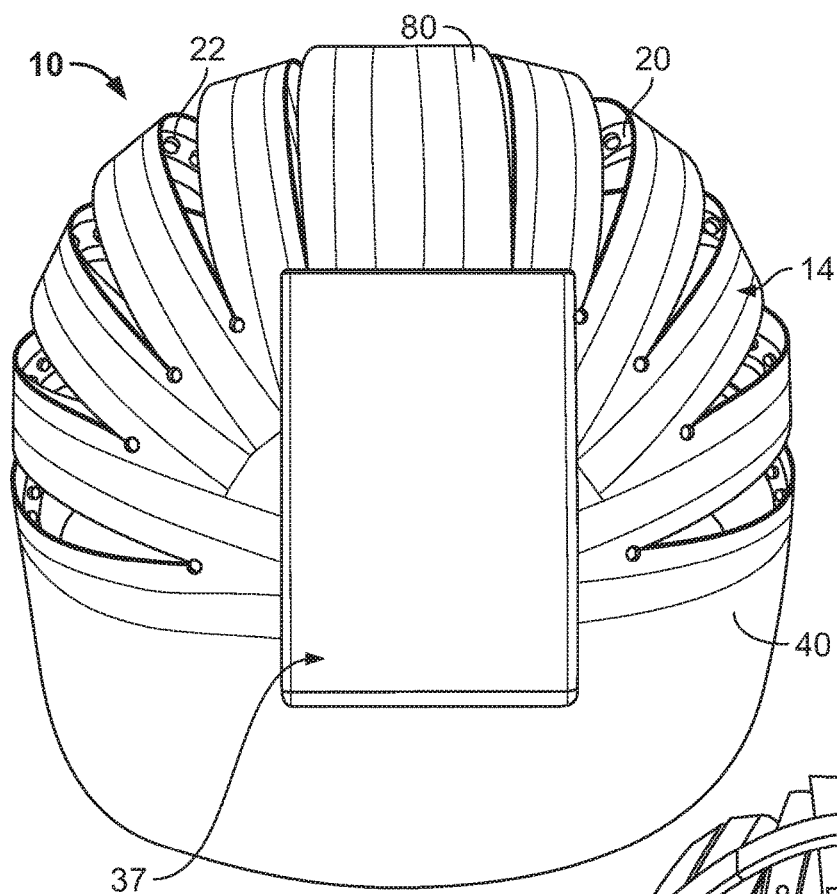
FIG. 1C is a back perspective view of the treatment device of FIG. 1A including an extension.
Figure 1D:
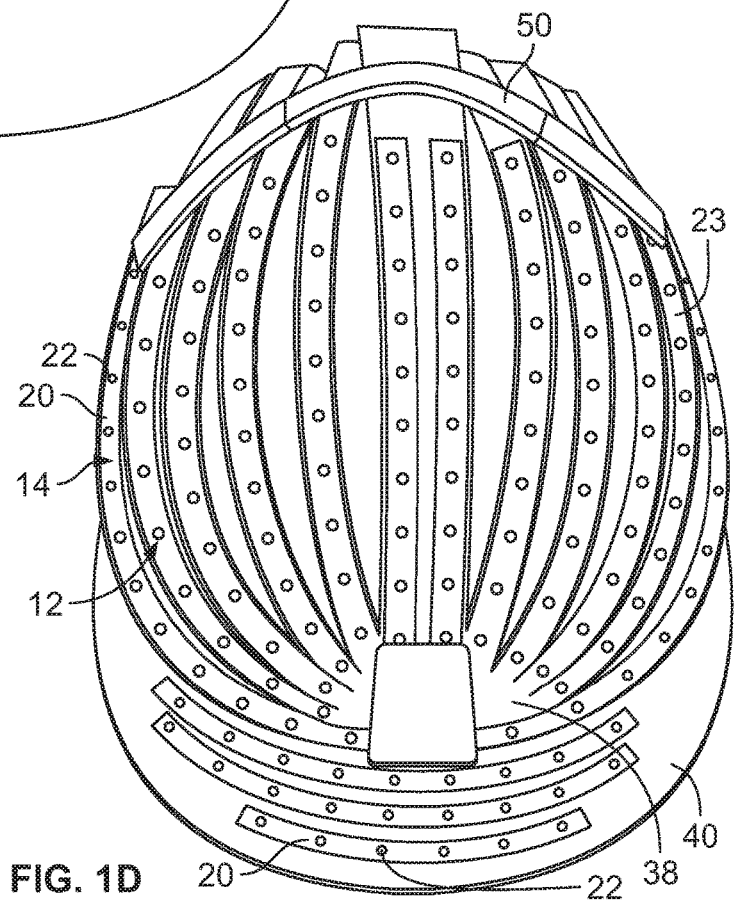
FIG. 1D is a perspective view of an interior of the treatment device of FIGS. 1A and 1C.

As shown in FIG. 1B, the outer layer 80 may include strain relief holes located near the point that two of the fingers of the fan shaped outer layer 80 join. The strain relief holes may act to alleviate bending of the fingers of the fan at these locations.

The linear light source strips 20 may be attached to the outer layer 80 via an adhesive layer 90. The adhesive layer 90 includes a first surface 92 that adheres to the back surface 16 of the array 14 and a second surface 94 opposite the first surface 92. The first surface 92 may adhere to the back surface of the array 14 upon contact (e.g., a pressure activated adhesive) or the first surface 92 may adhere to the back surface of the array 14 after the first surface 92 is activated (e.g., via heat, UV light, etc.). As an example, the adhesive layer 90 may comprise a pressure sensitive adhesive on the first surface 92 and the second surface 94 may comprise a heat activated adhesive.

Figure 4:
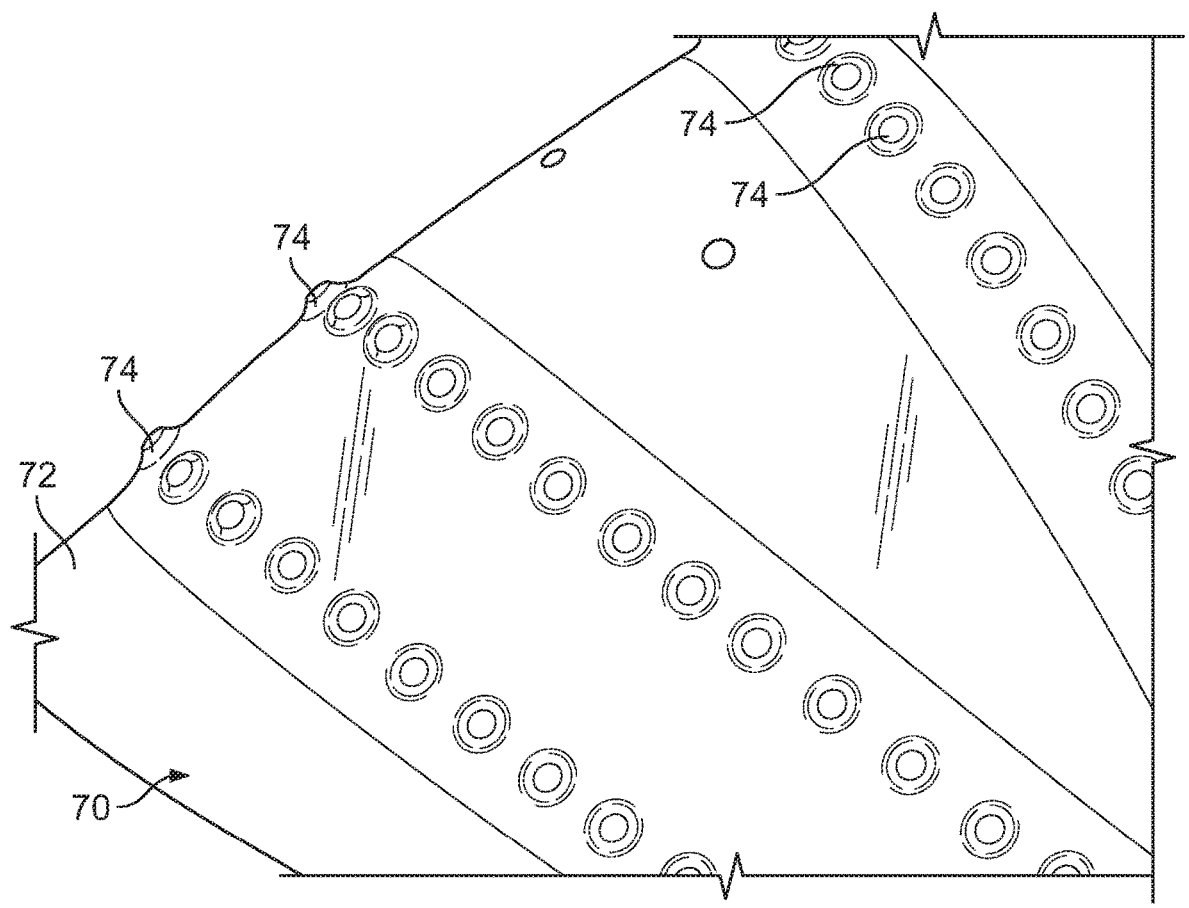
FIG. 4 is a close up view of an inner layer of FIGS. 2 and 3A.

Turning to FIGS. 4 and 5, the treatment device 10 may also include an inner layer 70. The inner layer 70 may be mounted adjacent an interior convex surface of the 3D surface 12. The inner layer 70 may serve a transparent protective covering, spacer, moisture barrier, etc. In addition, the inner layer 70 may act as a light diffuser to render the pattern of light emitted by the light sources 22 more uniform or to filter out certain undesired spectral components.

The inner layer 70 may include a surface 72 including a plurality of light covering elements 74 positioned to receive the light sources 22 of the linear light source strips 20. Each light covering element 74 may form a structure shaped to receive a light emission end 25 of one of the light sources 22 of the plurality of linear light source strips 20. For example, each light covering element 74 may project from the surface 72 of the inner layer 70 to form a hollow structure shaped to receive the light emission end 25 of one of the light sources 22 of the array 14. The light covering elements 74 may be configured to act as light guides to direct light emitted by the light sources away from the light sources.

In one embodiment, the light covering elements 74 may act to help the light emitted by the light sources 22 bypass a patient's hair and reach the patient's scalp. That is, when placed on a patient's head, the light covering elements 74 may project through a patient's hair such that a tip of each light covering element 74 rests on the patient's scalp. When light is emitted by a light source 22 associated with a particular light covering element 74, the light covering element 74 may direct the emitted light such that the emitted light is transmitted at an area of the light covering element 74 located near the tip of the light covering element 74. A further description of structures to deliver light passed the hair and to the scalp is disclosed in US 2010/0106077 A1 (Pub. Date: Apr. 29, 2010), which is hereby incorporated by reference in its entirety.

In some embodiments, the inner layer 70 may be configured to act as a diffuser to reflect, scatter, and/or refract light emitted by the light sources 22 in order to provide more uniform illumination. For example, the inner layer 70 may direct light emitted from the light sources 22 to a light scattering layer which then returns more uniform lighting to the inner layer 70 or alternatively to diffuse light by using a negative lens effect to cause the emitted light to diverge.

The light covering elements 74 may also act as a barrier between the light sources 22 and the patient's scalp. In one example, the barrier may provide protection for the light emitters and associated, wiring, circuitry, etc. As another example, by forming the light covering elements 74 of a soft rubber or plastic, the discomfort caused by the light sources 22 on the patient's scalp may be alleviated. As will be understood by one of ordinary skill in the art, the inner layer 70 may be made from any suitable material, such as silicone or any suitable plastic or rubber. The inner layer 70 may be thermoformed to create the light covering elements 74.

Figure 6A:
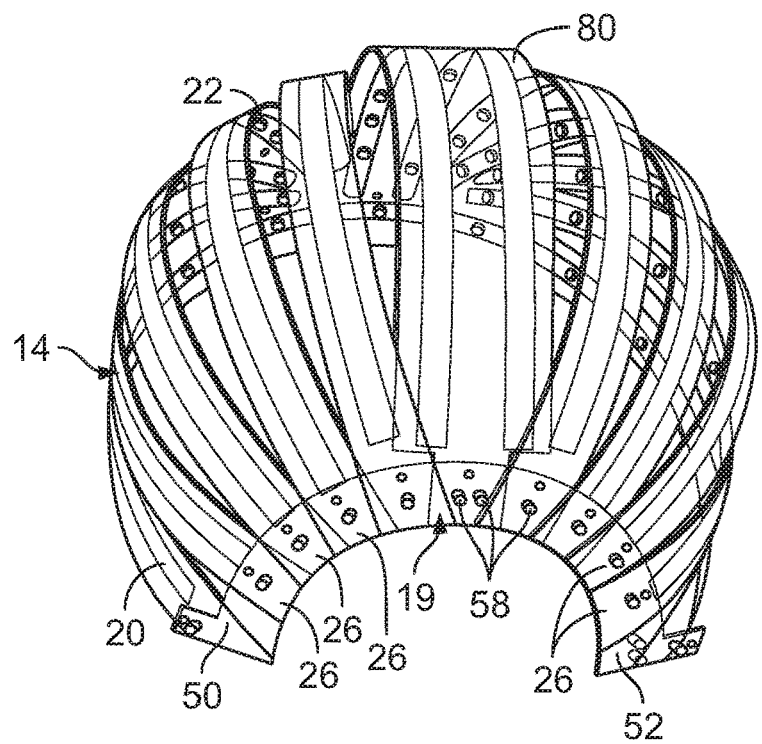
FIG. 6A is a perspective view of the treatment device of FIGS. 3A-3D and a joining member.
Figure 6B:
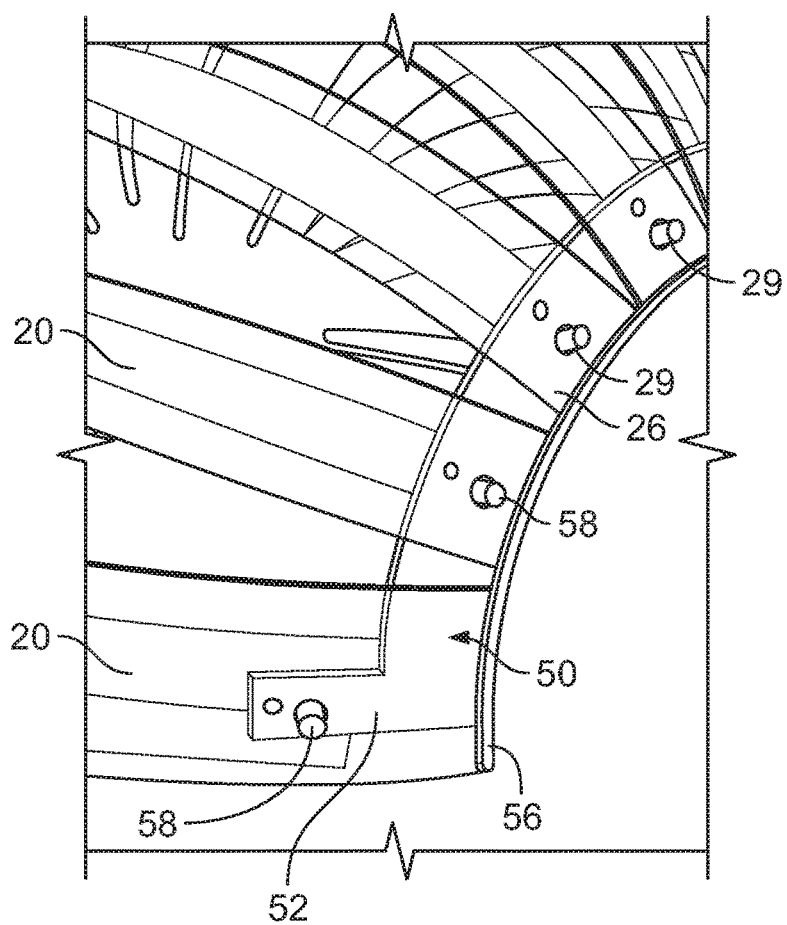
FIG. 6B is a close up view of the joining member of FIG. 6A.
Figure 6C:
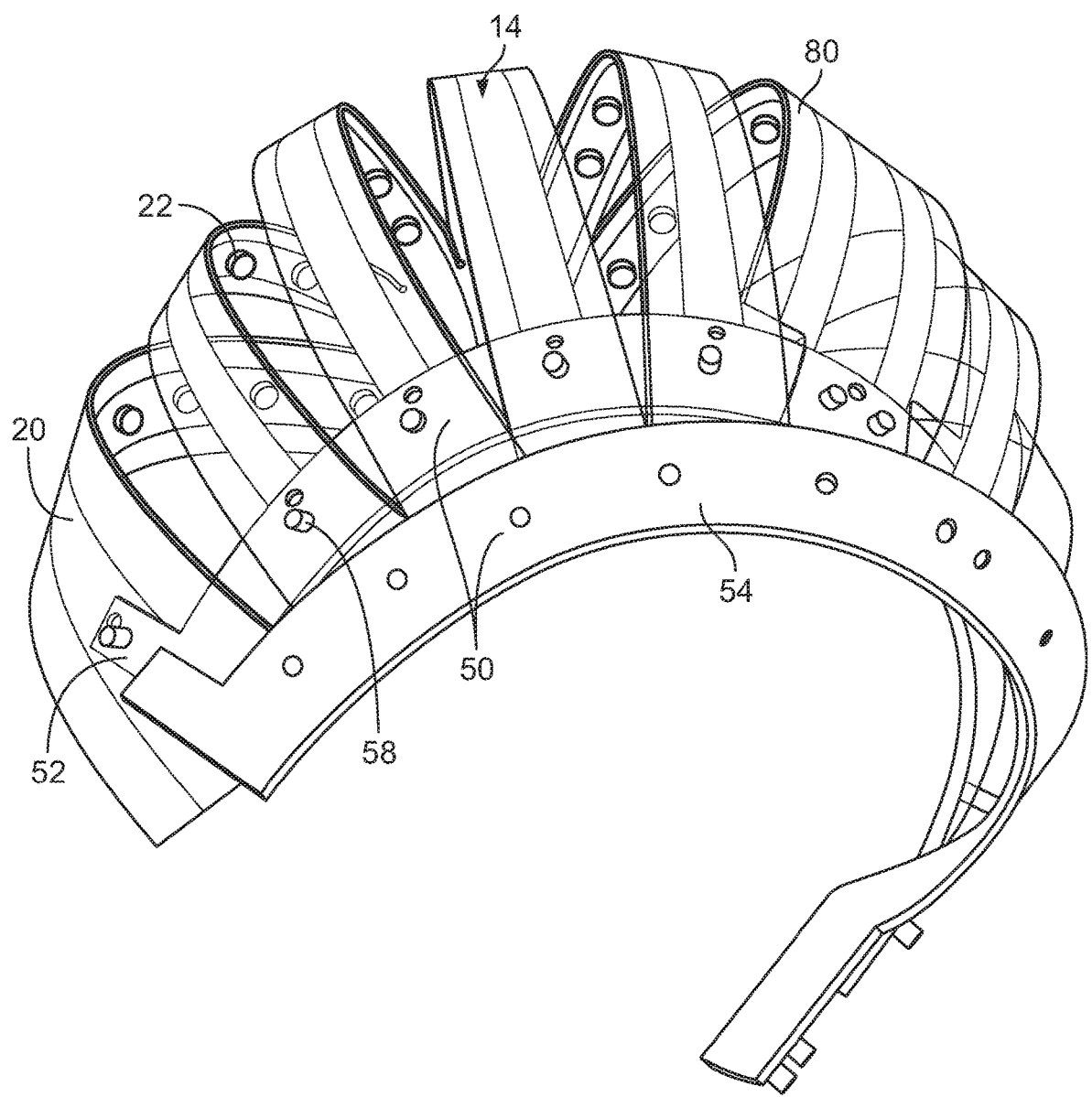
FIG. 6C is a close up view of the joining member of FIG. 6B and a cover portion of the joining member.

Turning to FIGS. 6A-6C, the termination point 26 of a majority of the linear light source strips 20 may be attached at the terminating end 19 to a joining member 50. The joining member 50 may comprise an arc-shaped slice as shown. The joining member 50 may be configured to receive and maintain the position of the linear light source strips 20, such that the position of the linear light source strip 20 are maintained in the formed 3D surface 12. For example, the joining member 50 may include an attachment portion 52 and a cover portion 54. The attachment portion 52 may include a receiving structure 56 configured to receive the terminating point 26 of each linear light source strip 20. The receiving structure 56 may maintain the position of the linear light source strip 26 through the interaction of projections 58 located in the receiving structure 56 and joining holes 29 in each linear light source strip. That is, projections 58 in the receiving structure 56 pass through holes 29 located in the terminating point 26 of each linear light source strip 20 and the projections 58 interact with the cover portion 54 to maintain the position of the linear light source strips 20. As shown in FIG. 6C, the projections 58 may interact with holes 59 to maintain the position of the attachment portion 52 and cover portion 54. As opposed to projections 58 and joining holes 29, the joining member 50 may maintain the position of the linear light source strip 20 using any suitable means. For example, the attachment portion 52 and the cover portion 54 may adhere to one another and maintain the position of the linear light source strips 20 via any suitable means (e.g., a mechanical fastener or chemical adhesive).

As will be understood by one of ordinary skill in the art, the joining member 50 may comprise any structure suitable for maintaining the position of the terminating end 19 of the linear light source strip 20. For example, the joining member 50 may comprise a rivet, pin, or similar structure that attaches the terminating end 19 of each linear light source strip 20 at the same point. In another example, the joining member 50 may comprise a rivet pin, or similar structure and the attachment portion 52 described above.

The controller circuitry 30 is electrically connected to each of the plurality of linear light source strips 20 to provide electrical power to each of the plurality of linear light source strips. The controller circuitry 30 controls illumination of a given linear light source strip 20 by providing electrical power to the given linear light source strip 20. For example, the controller circuitry 30 may be connected to the origination point 24 of each linear light source strip 20. Alternatively, the controller circuitry 30 may be connected to a single point on the array 14. As an example, the controller circuitry 30 may be connected to the array 14 near the origin point 18. For example, the light sources 22 may emit light in response to electric current.

The controller circuitry 30 may be electrically connected to the array 14 by electrically connecting the controller circuitry 30 to electrical leads supplying power to each of the linear light source strips 20. The controller circuitry 30 may be physically connected to the outer layer 80. Alternatively or additionally, the controller circuitry 30 may be embedded in the linear light source strips 20.

The controller circuitry 30 may be contained within a housing 37. The housing may comprise a receiving structure 38 and a covering structure 39. As shown in FIG. 3C, the receiving structure may include projections 41 that pass through holes 43 located in the controller circuitry 30 and the array 14. The projections 41 pass through the controller circuitry 30 and interact with the covering structure 39 to form the housing 37. The housing 37 may be made from any material suitable to protect the controller circuitry 30, such as plastic or metal or a combination of materials.

The controller circuitry 30 may include two more distinct sub-controllers. The sub-controllers may each comprise the hub of a subgroup of the plurality of linear light source strips. The controller circuitry 30 may be configured to provide power to the plurality of linear light source strips 20, such that the plurality of linear light source strips are illuminated in a pattern where all of the plurality of linear light source strips are not simultaneously illuminated.

For example, the controller circuitry 30 may include two sub-controllers that separately control a left half of the linear light source strips 20a-f and a right half of the linear light source strips 20g-1. By separating the linear light source strips 20 into at least two groups that are separately controlled, the controller circuitry 30 may cause the linear light source strips 20 to emit light at separate times. For example, a first group of linear light source strip 20a-20f may emit light together over a first duration of time. After the first duration of time, a second group of linear light source strips 20g-20l may be controlled to emit light together during a second duration of time that does not overlap with the first duration of time. Controlling the linear light source strip 20 such that only a portion of the linear light source strips 20 emit light at the same time may allow each of the light sources 22 to be supplied with more electrical power, resulting in an increased amount of light being emitted by each light source 22. In another example, the controller circuitry 30 is configured to individually and separately provide electrical power to each linear light source strip 20.

As will be understood by one of ordinary skill in the art, the controller circuitry 30 may have various implementations. For example, the controller circuitry 30 may include any suitable device, such as a processor, digital signal processor (DSP), Application Specific Instruction Set Processor (ASIP), Application Specific Integrated Circuit (ASIC), Field Programmable Gate Array (FPGA), programmable circuit, integrated circuit, memory and I/O circuits, an application specific integrated circuit, microcontroller, complex programmable logic device, other programmable circuits, or the like. The controller circuitry 30 may also include a non-transitory computer readable medium, such as random access memory (RAM), a read-only memory (ROM), an erasable programmable read-only memory (EPROM or Flash memory), or any other suitable medium. Instructions for controlling emission of light by the linear light source strip 20 may be stored in the non-transitory computer readable medium and executed by the circuitry.

The controller circuitry 30 may include a power supply for supplying electrical power to the controller circuitry 30 and the linear light source strip 20. The power supply may include a battery or a connecter to an external power supply. For example, the power supply may include a battery, a capacitor, any device capable of storing and providing electricity, or a connector to a wall outlet. In one embodiment, the power supply comprises a battery located adjacent the controller circuitry 30. The power supply may be replaceable and/or rechargeable.

Turning to FIGS. 1C, 1D, 3B, and 3D, an extension 60 may be added to the therapy device 10. In this scalp-illumination embodiment, the extension 60 provides light to a lower portion of the back of the head. The extension 60 may be formed as a separate piece from the array 14. For example, as shown in FIG. 3B, the extension 60 may include additional linear light source strips 20, a separate inner layer 20, adhesive 90, and outer layer 80. The extension 60 may be formed in the same manner as the array 14 described in FIG. 3A.

Figure 3D:
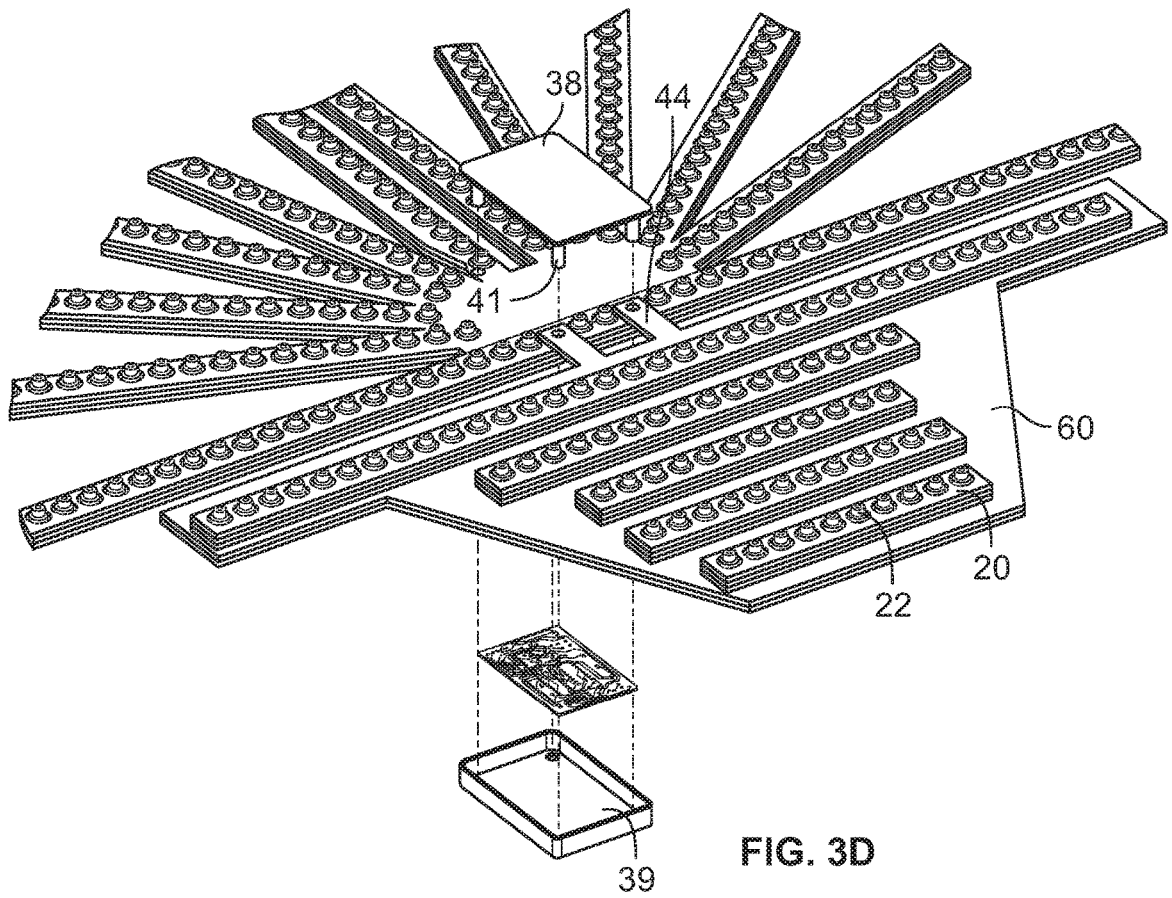
FIG. 3D is an exploded close up view of the treatment device of FIG. 3C and the extension panel of FIG. 3B.

The extension 60 may be attached to the device 10 of FIG. 3A by the controller housing 37. That is, the inner layer 70 may be positioned adjacent the extension layer 62 and the adhesive layer 90 may be placed between the extension layer 62 and the outer layer 80. The combination of the inner layer 70, extension board 62, adhesive layer 90, and outer layer 80 may include projections 64 having holes 43. The projections 62 may be placed over (as shown in FIG. 3D) or under the combination of the inner layer 70, array 14, adhesive layer 90, and outer layer 80, such that the holes 43 of the extension 60 overlap with the holes 43 of the array 14. The projections 41 may be passed through the holes 43 of the array 14, the extension 60, and the controller circuitry 30. The projections 41 pass through the holes 43 and interact with the covering structure 39 to maintain the position of the extension 60 relative to the array 14. Electrical contacts on the array 14 and the extension layer 60 may interact such that when the controller circuitry 30 is electrically connected to the array 14, the linear light source strips 20 of the extension 60 receive electrical power from the controller circuitry.

Figure 7:
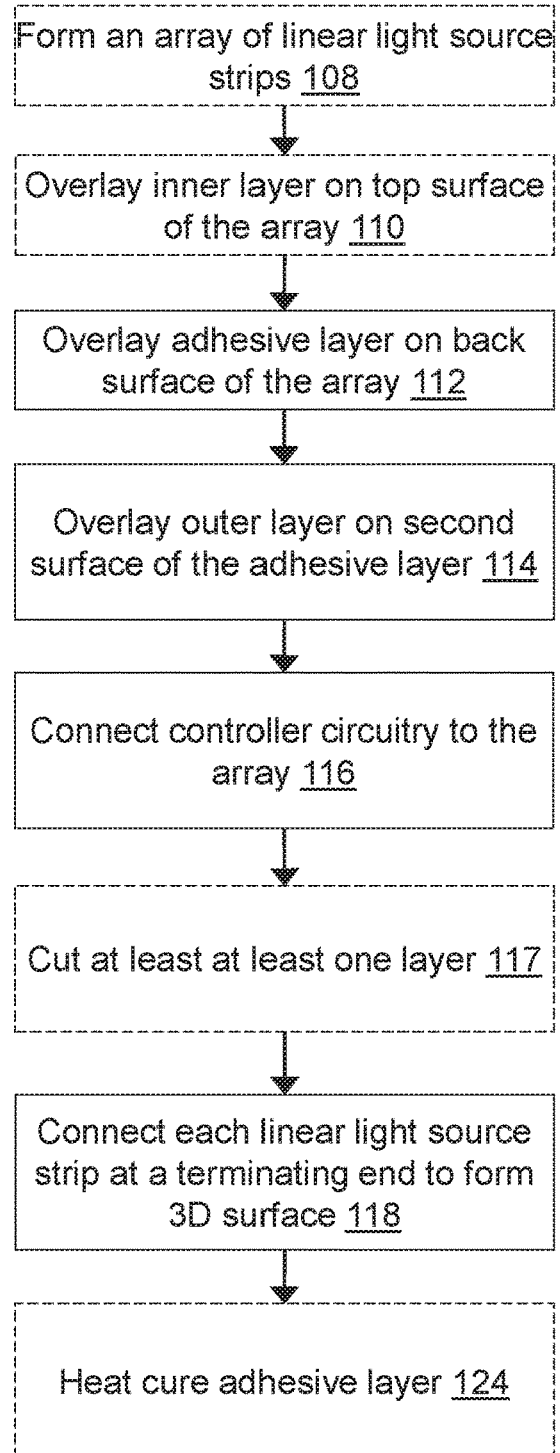
FIG. 7 is a flow chart of a method of manufacturing the treatment device.

Turning to FIGS. 2 and 7, the method 100 of manufacturing the treatment device may be performed using layers of materials. For example, sheets of materials may be arranged and processed in order to fabricate the treatment device 10 as described below. As will be understood by one of ordinary skill in the art, the steps described below in the manufacture of the treatment device 10 may be performed in different order.

Figure 3E:
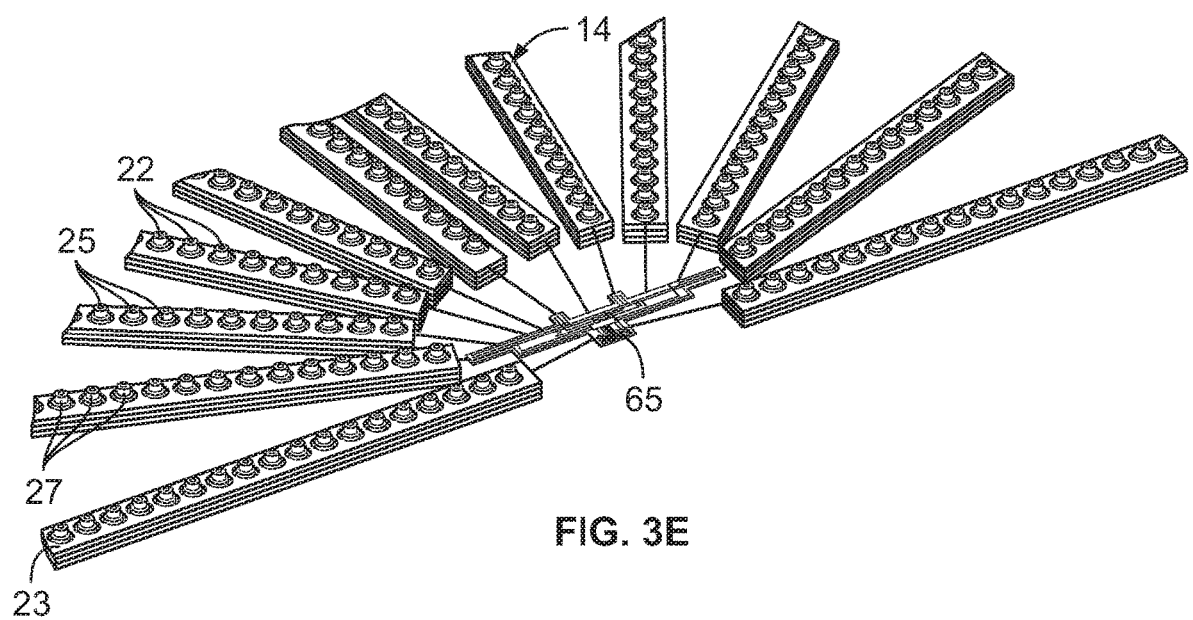
FIG. 3E is a perspective view of an alternative embodiment of the array.

Turning to FIGS. 3E and 7, prior to arranging the layers of materials, in optional process block 108 the array 14 of linear light source strips 20 may be formed by affixing separate linear light source strips 20 to an origin structure 65. For example, each separate linear light source strip may comprise prefabricated strips of LEDS. The linear light source strips 20 may be formed into an array 14 by mechanically and/or electrically connecting each linear light source strip 20 to the origin structure 65. For example, the linear light source strips 20 may be connected to the controller circuitry 30 by a wire. The origin structure 65 may comprise the controller circuitry 16, the outer layer 80, a sheet, substrate, printed circuit board, or any other suitable structure. In another embodiment, the light source strips 20 are manufactured aggregately as one or more flexible printed circuit boards which may also include sub controllers and/or other circuit components. The flexible board may be die cut prior to or after population with circuit elements.

In optional process block 110, an inner layer 70 is overlayed on a top surface 15 of the array 14. As described previously, the inner layer 70 comprises a surface 72 including a plurality of light covering elements 74 positioned to receive the light sources 22 of the array 14. Overlaying the inner layer 70 on the front surface 15 of the array 14 includes positioning the light emission end 25 of each of the light sources 22 of the array 14 into a light covering element 74 projecting from the surface 72 of the inner layer 70. The inner layer 70 may be fastened to the array 14 via any suitable means.

In process block 112, an adhesive layer 90 is overlayed on a back surface 16 of the array 14 of a plurality of linear light source strips 20, such that the adhesive layer 90 adheres to the back surface 16 of the array 14. Prior to overlying the adhesive layer 90 on the back surface 16 of the array 14, a mask layer may be overlayed on the back surface 16 of the array 14. The mask layer may include a surface shaped to cover the base end 27 of the light sources 22 of the array 14, such that the adhesive layer 90 is prevented from adhering with the base end 27 of the light sources 22 by the mask layer when the adhesive layer 90 is combined with the back surface 16 of the array 14.

In process block 114, an outer layer 80 is overlayed on the second surface 94 of the adhesive layer 90. As described previously, the second surface 94 may include an adhesive that must be activated before adhering to the outer layer 80. That is, the second surface 94 may not adhere to the outer layer 80 during this stage of manufacturing the treatment device 10.

In process block 116, the controller circuitry 30 is connected to the array 14. The controller circuitry 30 may be electrically and/or physically connected to the array 14. For example, the controller circuitry 30 may be soldered onto electrical connections of the array 14 in order to electrically connect the array 14 and the controller circuitry 30. The controller circuitry 30 may be physically connected to the array 14 via the housing 37. As described previously, the housing 37 may be connected to the array by passing projections 41 through holes 43 located in at least one of the controller circuitry 30, inner layer 70, outer layer 80, adhesive layer 90, and the array 14. The projections 41 pass through the holes 43 and interact with the covering structure 39 to form maintain the position of the controller circuitry 30 relative to the array 14. The controller circuitry 30 may alternatively or additionally be physically connected to the array 14 via mechanical or chemical fixation.

In process block 118, each linear light source strip 20 is connected at a terminating end 19 opposite the origin point 18, such that the linear light source strips 20 of the array 14 are arranged to form a three-dimensional (3D) surface 12 such that the combined light emitted by the light sources 22 of the plurality of linear light source strips 20 illuminates the surface of the 3D skin surface when positioned adjacent the 3D skin surface. For example, each linear light source strip 20 may be connected at the terminating end 19 to a joining member 50 as described above. Connecting the linear light source strips 20 to the joining member 50 may include positioning the terminating point 26 of each linear light source strip 20 in a receiving structure 52 of the joining member 50 such that the linear light source strip 20 are maintained in the formed 3D surface 12. The terminating point 26 of each linear light source strip 26 may be positioned in the receiving structure 52, such that projections 54 located within the receiving structure 52 of the joining member 50 interact with the joining hole 29 of each linear light source strip.

In optional process block 117, prior to connecting each linear light source strip at the terminating end, at least one of the array 14, adhesive layer 90, or outer layer 80 is cut. For example, the combination of the array 14, adhesive layer 90, and outer layer 80 may be cut. As will be understood by one of ordinary skill in the art, the at least one of the array 14, adhesive layer 90, or outer layer 80 may be die cut, laser cut, or cut using any suitable means. For example, FIG. 2 shows the different layers assembled prior to being cut and FIG. 3A shows the different layers assembled after being cut. The cutting may also include forming a joining hole 29 in at least one the terminating end 19 of each linear light source strips 20 opposite the origin point 18, the outer layer 80, the adhesive layer 90, or the inner layer 70. Each linear light source strip 20 may be joined to the joining member 50 via the joining hole 29.

As shown in FIGS. 2 and 3A, prior to cutting the array 14 may comprise a sheet including a plurality of light sources 22 positioned such that the plurality of light sources 22 form the plurality of linear light source strips 20 when the array 14 is cut. Devices 10 having different circumferences (e.g., in order to fit different sized heads) may be formed by cutting the linear light source strips 20, outer layer 80, inner layer 70, and/or adhesive layer 90 to different lengths. Manufacturing the device 10 in this manner allows different sized devices 10 to be manufactured by simply changing the die used to perform the cutting.

In optional process block 124, the adhesive layer 90 is heat cured after connecting each linear light source strip 20 at the terminating end 19 to adhere the outer layer 80 and the adhesive layer 90.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms used to describe such components are intended to correspond, unless otherwise indicated, to any component which performs the specified function of the desired component (e.g., that is functionally equivalent), even though not structurally equivalent to the disclosed component which performs the function of the herein disclosed exemplary embodiment of the invention. In addition, while a particular feature of the invention may have been disclosed with respect to only one embodiment, such feature may be combined with one or more other features as may be desired and advantageous for any given or particular application.

What is claimed is:

1. A medical or cosmetic treatment device configured to illuminate a surface of a 3D skin surface when positioned adjacent the illuminated surface of the 3D skin surface, the medical or cosmetic treatment device comprising:
   a plurality of linear light source strips, wherein:
      each linear light source strip includes a plurality of light sources;
      each linear light source strip has an origination point and a termination point;
      for a given linear light source strip, each light source of the given linear light source strip is arranged between the origination point and the termination point;

controller circuitry electrically connected to each of the plurality of linear light source strips, wherein:

the controller circuitry is configured to provide electrical power to each of the plurality of linear light source strips; and a joining member configured to attach to the termination point of a majority of the plurality of linear light source strips, such that:

the plurality of linear light source strips are arranged to form a three-dimensional (3D) surface; and the combined light emitted by the light sources of the plurality of linear light source strips illuminates the surface of the 3D skin surface when positioned adjacent the 3D skin surface;

wherein the plurality of linear light source strips are arranged in a fan like shape and, within the fan like shape, the linear light source strips are arranged in a palmate pattern on a concave interior surface of a supporting 3D concave shape.

2. The medical or cosmetic treatment device of claim 1, wherein the controller circuitry comprises a hub of the fan like shape.

3. The medical or cosmetic treatment device of claim 2, wherein the controller circuitry comprises two more distinct sub-controllers and the sub-controllers each comprise the hub of a subgroup of the plurality of linear light source strips.

4. The medical or cosmetic treatment device of claim 1, wherein the linear light source strips have different lengths.

5. The medical or cosmetic treatment device of claim 1, wherein the spacing between at least some of the adjacent linear light source strips is adjustable.

6. The medical or cosmetic treatment device of claim 1, wherein the joining member comprises an arc-shaped slice.

7. The medical or cosmetic treatment device of claim 1, wherein the plurality of linear light source strips are arranged such that the plurality of linear light source strips do not overlap.

8. The medical or cosmetic treatment device of claim 1, wherein the 3D surface is adjustable to illuminate the surface of 3D skin surfaces having different sizes.

9. The medical or cosmetic treatment device of claim 1, wherein the controller circuitry is configured to individually and separately provide electrical power to each linear light source strip.

10. The medical or cosmetic treatment device of claim 1, wherein the controller circuitry is configured to provide power to the plurality of linear light source strips, such that the plurality of linear light source strips are illuminated in a pattern where all of the plurality of linear light source strips are not simultaneously illuminated.

11. The medical or cosmetic treatment device of claim 1, further comprising a power supply configured to supply electrical power to the controller circuitry.

12. The medical or cosmetic treatment device of claim 11, wherein the power supply comprises a battery or a connector to an external power supply.

13. The medical or cosmetic treatment device of claim 11, wherein the power supply comprises a battery located adjacent the controller circuitry.

14. The medical or cosmetic treatment device of claim 1, wherein the plurality of light sources are either laser diodes, light emitting diodes (LEDs), or a combination of laser diodes and LEDs.

15. The medical or cosmetic treatment device of claim 1, wherein the plurality of light sources emit electromagnetic radiation within a range of wavelengths or set of wavelengths having a known therapeutic effect.

16. The medical or cosmetic treatment device of claim 15, wherein the plurality of light sources emit electromagnetic radiation having wavelengths chosen from at least one of the set of ultraviolet, visible, and infrared.

17. The medical or cosmetic treatment device of claim 15, wherein the plurality of light sources collectively emit electromagnetic radiation having wavelengths in two different wavelength ranges, each light source emitting light in only one of the two different wavelength ranges.

18. The medical or cosmetic treatment device of claim 17, wherein the two different wavelength ranges are chosen from at least one of the set ultraviolet, visible, and infrared.

19. The medical or cosmetic treatment device of claim 1, further comprising a light diffuser, wherein:

the light diffuser includes a surface;

the plurality of linear light source strips are mounted adjacent the surface of the light diffuser;

each light source of the plurality of linear light source strips emits electromagnetic radiation towards the diffuser;

the light diffuser is configured to reflect, scatter, and/or refract light in order to provide uniform illumination to the surface of the 3D skin surface.

20. The medical or cosmetic treatment device of claim 1, further comprising a diffuser, wherein:

the diffuser is mounted adjacent an interior convex surface of the 3D surface;

each light source of the plurality of linear light source strips emits electromagnetic radiation towards the diffuser;

the diffuser is configured to scatter and/or refract light in order to provide uniform illumination to the surface of the 3D convex skin surface.

21. The medical or cosmetic treatment device of claim 1, further comprising an inner layer comprising a surface including a plurality of light covering elements positioned to receive the light sources of the linear light source strips, wherein each light covering element forms a structure shaped to receive a light emission end of one of the light sources of the plurality of linear light source strips.

22. The medical or cosmetic treatment device of claim 21, wherein the light covering elements are configured to act as light guides to direct light emitted by the light sources away from the light sources.

23. A method of manufacturing treatment device configured to illuminate a surface of a 3D skin surface, the method comprising: overlying an adhesive layer on a back surface of an array of a plurality of linear light source strips, such that the adhesive layer adheres to the back surface of the array, wherein: each linear light source strip of the plurality of linear light source strips includes a plurality of light sources connected to a substrate; the substrate forms a back surface of the array; each light source includes a light emission end and a base end opposite the light emission end; the base end of each light source is connected to the substrate; each of the plurality of linear light source strips are connected to an origin point of the array; the linear light source strips fan out from the origin point; the adhesive layer includes a first surface that adheres to the back surface of the array and a second surface opposite the first surface; overlying an outer layer on the second surface of the adhesive layer; connecting controller circuitry to the array, wherein the controller circuitry provides electrical power to the light sources of the array; connecting to a joining member each linear light source strip at a terminating end opposite the origin point, such that the linear light source strips of the array are arranged to form a three-dimensional (3D) surface such that the combined light emitted by the light sources of the plurality of linear light source strips illuminates the surface of the 3D skin surface when positioned adjacent the 3D skin surface; wherein the plurality of linear light source strips are arranged in a fan like shape and, within the fan like shape, the linear light source strips are arranged in a palmate pattern on a concave interior surface of a supporting 3D concave shape.

24. The method of claim 23, further comprising:
overlying an inner layer on a front surface of the array, wherein the inner layer comprises a surface including a plurality of light covering elements positioned to receive the light sources of the array.

25. The method of claim 24, wherein overlying the inner layer on the front surface of the array includes positioning the light emission end of each of the light sources of the array into a light covering element projecting from the surface of the inner layer.

26. The method of claim 23, wherein the adhesive layer comprises:
a pressure sensitive adhesive on the first surface that is applied to the back surface of the array;
a heat activated adhesive or a second pressure sensitive adhesive on the second surface that is applied to the outer layer.

27. The method of claim 26, further comprising heat curing the adhesive layer after connecting each linear light source strip at the terminating end to adhere the outer layer and the adhesive layer.

28. The method of claim 23, wherein at least one of the array, adhesive layer, or outer layer is die cut or laser cut.

29. The method of claim 23, wherein each linear light source strip is connected at the terminating end to a joining member.

30. The method of claim 29, further comprising:
prior to connecting each linear light source strip to the joining member, cutting the combination of the array, adhesive layer, and outer layer, wherein the cutting comprises:
forming a joining hole at the terminating end of each linear light source strip opposite the origin point, wherein each linear light source strip is joined to the joining member via the joining hole.

31. The method of claim 30, wherein:
prior to cutting the array, adhesive layer, and outer layer, the array of linear light source strips comprises a sheet including a plurality of light sources positioned such that the plurality of light sources form the plurality of linear light source strips when the array is cut.

32. The method of claim 31, wherein:
the joining member comprises an arc-shaped slice; and
connecting the linear light source strips to the joining member comprises positioning a terminating point of each linear light source strip in a receiving structure of the joining member such that projections located within the receiving structure of the joining member interact with the joining hole of each linear light source strip.

33. The method of claim 23, wherein:
the joining member comprises an arc-shaped slice;
connecting the linear light source strips to the joining member comprises positioning the terminating end of each linear light source strip in a receiving structure of the joining member such that the linear light source strips are maintained in the formed 3D surface.

34. The method of claim 23, wherein the array of linear light source strips is formed by affixing separate linear light source strips to an origin structure.

35. The method of claim 23, wherein the array of linear light source strips is symmetric about a central axis perpendicular to one or more base linear light source strips.

36. The method of claim 23, wherein the controller circuitry is connected to the light source strip array near the origin point.

37. The method of claim 23, wherein the controller circuitry is connected to the array by electrically connecting the controller circuitry to electrical leads supplying power to each of the plurality of linear light source strips.

38. The method of claim 23, wherein the controller circuitry is physically connected to the outer layer.

* * * * *